United States Patent [19]

Mandai et al.

[11] Patent Number: 5,322,939
[45] Date of Patent: Jun. 21, 1994

[54] PROCESS FOR PREPARING AZETIDIN-2-ONE DERIVATIVES

[75] Inventors: Tadakatsu Mandai; Jiro Tsuji, both of Okayama, Japan

[73] Assignee: Takasago International Corporation, Tokyo, Japan

[21] Appl. No.: 909,678

[22] Filed: Jul. 7, 1992

[30] Foreign Application Priority Data

Jul. 15, 1991 [JP] Japan .................. 3-199988

[51] Int. Cl.$^5$ .................. C07D 205/08; C07B 43/06
[52] U.S. Cl. .................. 540/200; 540/362; 556/413; 558/275; 558/276; 560/29; 564/93
[58] Field of Search .................. 540/200, 362

[56] References Cited

PUBLICATIONS

Hackh's Chemical Dictionary, 3rd Edition p. 33 (1944).
Chiba, Tetrahedron, 41, 387 (1985).
Synlett, No. 2, Feb. 1991, pp. 91–92.
Tetrahedron Letters, vol. 32, No. 52, Dec. 23, 1991, pp. 7683–7686 Mandai et al.
Journal of the American Chemical Society, Jul. 18, 1979, pp. 4107–4119.
Oxford Dictionary Suppl. (1972) p. 21.
McGraw Hill Dictionary, 4th Edition p. 30.
*Tetrahedron Letters*, 29, pp. 5053–5056 (1988).
*J. Chem. Soc., Chem. Commun.* pp. 294–296 (1990).
*J. Chem. Soc., Chem. Commun.* pp. 1066–1067 (1984).
*J. Chem. Soc. Chem. Commun.* pp. 735–737 (1987).
*Tetrahedron Letters*, 29, pp. 2765–2768 (1988).
*J. Org. Chem.* 52 pp. 1315–1319 (1987).
*Chem. Soc., Rev.*, 5, pp. 181–202 (1976).
*J. Chem. Soc., Chem. Commun.*, pp. 698–699 (1979).

*Primary Examiner*—Mark L. Berch
*Attorney, Agent, or Firm*—Sughrue, Mion, Zinn, Macpeak & Seas

[57] ABSTRACT

A process for preparing an azetidin-2-one derivative represented by formula (2):

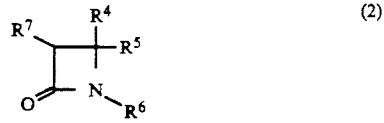

wherein $R^4$ and $R^5$, which may be the same or different, each represents a hydrogen atom, an alkyl group having from 1 to 8 carbon atoms, or an alkyl group having from 1 to 8 carbon atoms substituted with an alkoxy group, an acyl group, or an alkoxycarbonyl group; $R^6$ represents a protective group for an amino group; and $R^7$ represents a vinylidene group of formula

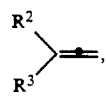

or an acetylene group of formula

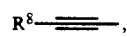

wherein $R^2$ and $R^3$, which may be the same or different, each represents a hydrogen atom or an alkyl group having from 1 to 8 carbon atoms; and $R^8$ represents an alkyl group having from 1 to 8 carbon atoms corresponding to $R^2$ or $R^3$, which comprises reacting a propargyl alcohol derivative represented by formula (1):

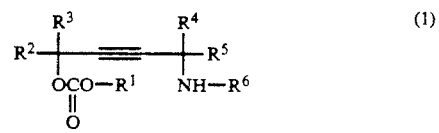

wherein $R^1$ represents an alkyl group having from 1 to 6 carbon atoms, a phenyl group, or a halogen-substituted phenyl group; $R^2$, $R^3$, $R^4$, $R^5$, $R^6$ and $R^7$ are as defined above, with carbon monoxide in the presence of a palladium complex. The compound (2), an intermediate of penem antibiotics, can be obtained through one reaction step in good yield.

6 Claims, No Drawings

PROCESS FOR PREPARING AZETIDIN-2-ONE DERIVATIVES

FIELD OF THE INVENTION

This invention relates to a process for preparing a useful intermediate for synthesizing β-lactam antibiotics, for example, penem antibiotics exemplified by thienamycin. More particularly, it relates to a process for preparing an azetidin-2-one derivative represented by formula (2):

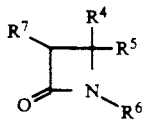
(2)

wherein $R^4$ and $R^5$, which may be the same or different, each represents a hydrogen atom, an alkyl group having from 1 to 8 carbon atoms, or an alkyl group having from 1 to 8 carbon atoms substituted with an alkoxy group, an acyl group, or an alkoxycarbonyl group; $R^6$ represents a protective group for an amino group; and $R^7$ represents a vinylidene group of formula

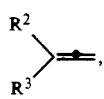

or an acetylene group of formula

wherein $R^2$ and $R^3$, which may be the same or different, each represents a hydrogen atom or an alkyl group having from 1 to 8 carbon atoms; and Rs represents an alkyl group having from 1 to 8 carbon atoms corresponding to $R^2$ or $R^3$.

BACKGROUND OF THE INVENTION

β-Lactam antibiotics represented by thienamycin have derives weight as medicines from their broad antimicrobial spectra, and various types of β-lactam antibiotics have been studied.

Among the developed β-lactam antibiotics, those having a vinylidene group or an acetylene group at the 3-position of the azetidin-2-one skeleton have recently attracted attention (refer to *Tetrahedron Lett.*, Vol. 29, p. 5053 (1988), *J. Chem. Soc., Chem. Commun.*, p. 294 (1990), and ibid., p. 1066 (1984)). There has been a demand, accordingly, for an industrially advantageous process for preparing an azetidin-2-one derivative having a vinylidene group or an acetylene group at the 3-position which is an intermediate for synthesizing β-lactam antibiotics of this type.

Known processes for preparing azetidin-2-one derivatives having a vinylidene group at the 3-position include a process shown in reaction scheme A below, which comprises alkylating the nitrogen atom of a 3-alkylidene-azetidin-2-one compound, chlorinating the product with t-butyl hypochlorite, and subjecting the resulting compound to desilylation and dechlorination simultaneously to prepare a 3-vinylidene-azetidin-2-one derivative in a percent yield of from 36 to 68% (refer to *J. Chem. Soc.. Chem. Commun.*, p. 735 (1987)).

Reaction Scheme A:

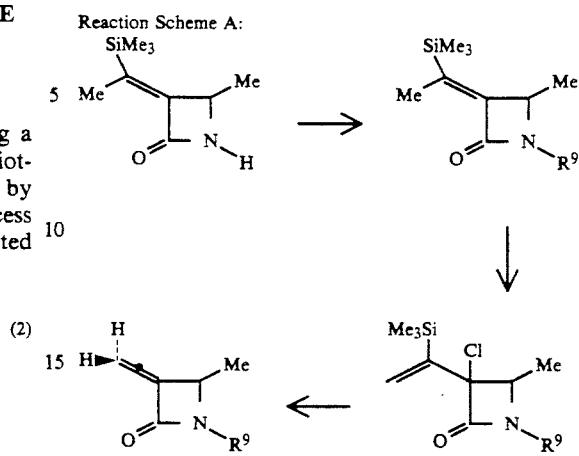

wherein Me represents a methyl group; and $R^9$ represents a methyl group, a benzyl group, or a substituted benzyl group.

Known processes for preparing azetidin-2-one derivatives having an acetylene group at the 3-position include a process shown in reaction scheme B below, which comprises reacting a di(phenylacetyl)cyclohexadiene derivative with zinc chloride in a carbon tetrachloride solvent to obtain a bicyclo[2.2.2]octadienone derivative in a percent yield of 60%, thermally decomposing the product to obtain an alkenylketene, and reacting the alkenylketene with N-phenylbenzylideneimine to obtain the desired compound in a yield of 72% (refer to *Tetrahedron Lett.*, Vol. 29, p. 2765 (1988)); and a process shown in reaction scheme C below, which comprises reacting a 2,5-dialkynyl-3,6-dichloro-1,4-benzoquinone with an azide ion to obtain a diazidoquinone and reacting the resulting compound in a carbon tetrachloride solvent in the presence of dicyclohexylcarbodiimide (DCC) to obtain a desired compound with the percent yield of the latter reaction being from 42 to 86% (refer to *J. Org. Chem.*, Vol. 52, p. 1315 (1987) and *J. Chem. Soc., Chem. Commun.*, p. 1066 (1984)).

Reaction Scheme B:

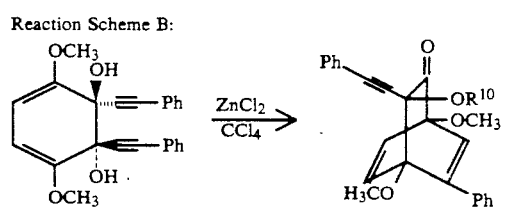

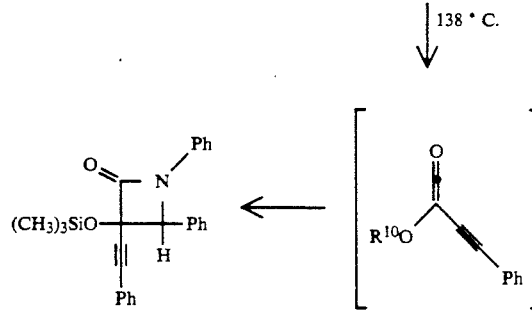

wherein $R^{10}$ represents a hydrogen atom or a trimethylsilyl group; and Ph represents a phenyl group.

Reaction Scheme C:

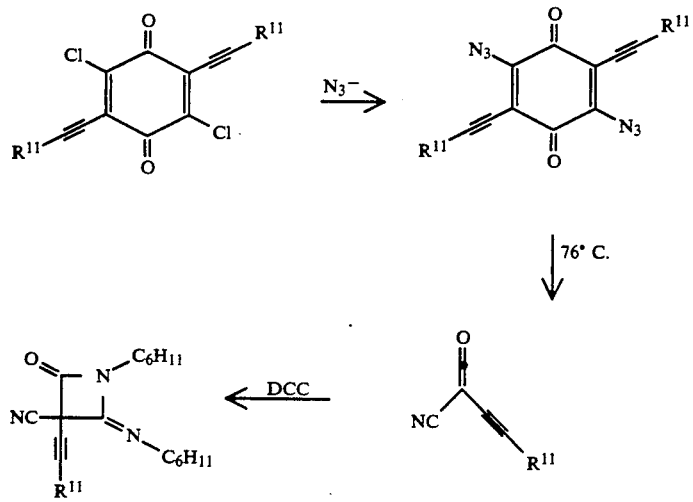

wherein $R^{11}$ represents an n-butyl group, a phenyl group, a substituted phenyl group, a phenethyl group, etc.

However, any of these known processes involves long reaction steps and is therefore not suitable for industrial production.

It is known, on the other hand, that β-lactam compounds are synthesized through various techniques, such as cyclization of a β-amino acid, cyclization of a halogenated propanamide, reaction between an enol silyl ether and chlorosulfonyl isocyanate, and reaction between an imine and a diketene (refer to *Chem. Soc. Rev.*, Vol. 5, p. 181 (1976), *YUKI GOSEI KAGAKU*, Vol. 47, p. 606 (1989), etc.). Among these known processes is included a process shown in reaction scheme D, in which a 2-bromo-3-aminopropene derivative is reacted with carbon monoxide to conduct carbonylation and lactamization at the same time (refer to *J. Chem. Soc., Chem. Commun.*, p. 698 (1979)).

Reaction Scheme D:

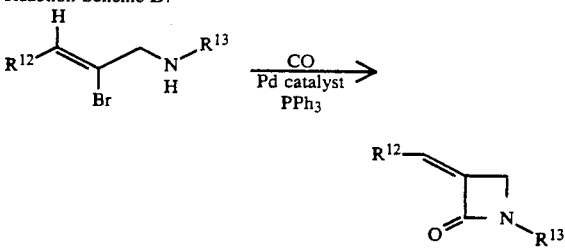

wherein $R^{12}$ a hydrogen atom or a phenyl group; $R^{13}$ represents a benzyl group, a phenethyl group, etc.; and Ph represents a phenyl group.

SUMMARY OF THE INVENTION

An object of the present invention is to provide a process for preparing an azetidin-2-one derivative having a vinylidene group or an acetylene group at the 3-position through simple and easy operation in good yield.

As a result of extensive investigations, the inventors have found that the above object of the present invention can be accomplished by reacting a propargyl alcohol derivative with carbon monoxide in the presence of a palladium complex. The present invention has been completed based on this finding.

The process according to the present invention is illustrated by reaction scheme E shown below.

Reaction Scheme E:

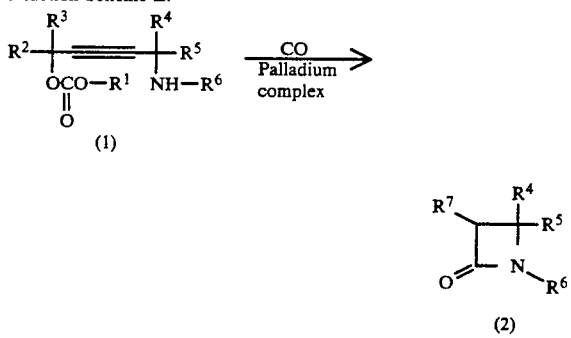

wherein $R^{100}$ represents an alkyl group having from 1 to 6 Carbon atoms, a phenyl group, or a halogen-substituted phenyl group; $R^2$, $R^3$, $R^4$, $R^5$, $R^6$, and $R^7$ are as defined above.

That is, the present invention relates to a process for preparing an azetidin-2-one derivative represented by formula (2) comprising reacting a propargyl alcohol derivative represented by formula (1) with carbon monoxide in the presence of a palladium complex.

DETAILED DESCRIPTION OF THE INVENTION

In formula (1) the alkyl group having from 1 to 6 carbon atoms represented by $R^1$ includes methyl, ethyl, propyl, isopropyl, butyl, isobutyl, pentyl, isopentyl, and hexyl groups; and the halogen-substituted phenyl group represented by $R^1$ includes 4-bromophenyl, 4-chlorophenyl, and 4-fluorophenyl groups.

The alkyl group having from 1 to 8 carbon atoms represented by $R^2$ and $R^3$ includes methyl, ethyl, propyl, isopropyl, butyl, t-butyl, sec-butyl, pentyl, hexyl, heptyl, and octyl groups.

The alkyl group having from 1 to 8 carbon atoms represented by $R^4$ or $R^5$ includes methyl, ethyl, propyl, isopropyl, butyl, t-butyl, sec-butyl, pentyl, hexyl, heptyl, and octyl groups. The alkoxy group substituting the alkyl group includes methoxy and ethoxy groups; the acyl group substituting the alkyl group includes formyl, acetyl, and benzoyl groups; and the alkoxycarbonyl group substituting the alkyl group includes methoxycarbonyl, ethoxycarbonyl, and t-butyoxycarbonyl groups.

The protective group for an amino group represented by $R^6$ is not particularly limited and includes benzyl, tosyl, acyl, p-methoxybenzyl, and biphenylmethyl groups.

The starting compound, propargyl alcohol derivative of formula (1), can be obtained, for example, by reacting a β-aminoacetylene derivative with a carbonyl compound to obtain a β-aminoalkyl-substituted propargyl alcohol derivative, which is then reacted with a halogenated formic ester as shown by reaction scheme F:

Reaction Scheme F:

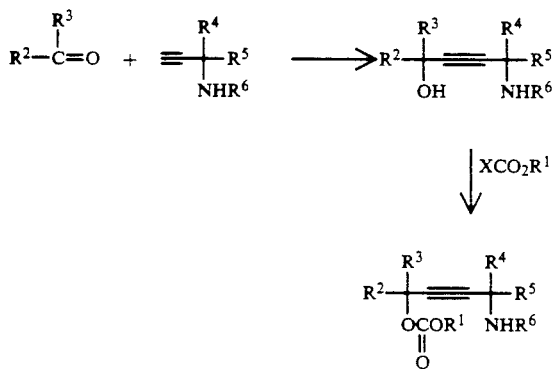

wherein $R^1$, $R^2$, $R^3$, $R^4$, $R^5$, and $R^6$ are as defined above.

The propargyl alcohol derivative of formula (1) can also be obtained by reacting a silyl-protected propargyl alcohol derivative with an imine to obtain a β-aminoalkyl-substituted propargyl alcohol derivative (refer to *Tetrahedron Lett.*, Vol. 25, p. 1083 (1984)), protecting the amino group of the product by an appropriate protective group, removing the silyl group protecting the hydroxyl group, and then reacting the resulting compound with a halogenated formic ester as shown in reaction scheme G:

Reaction Scheme G:

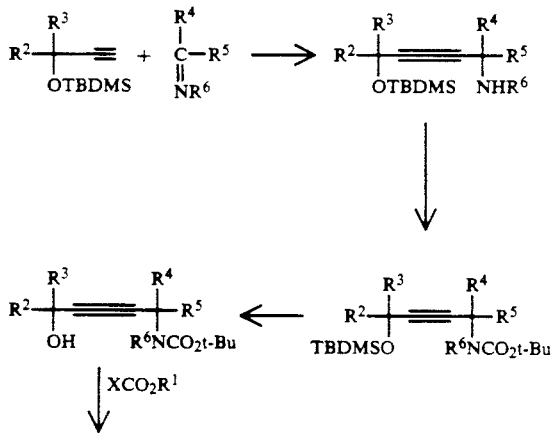

Reaction Scheme G:

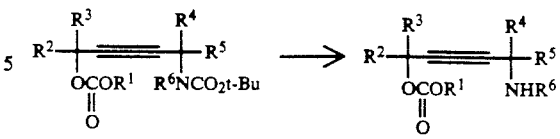

wherein $R^1$, $R^2$, $R^3$, $R^4$, $R^5$, and $R^6$ are as defined above; and TBDMS represents a t-butyldimethylsilyl group.

When starting with a propargyl alcohol derivative of formula (1) wherein $R^2$ and $R^3$ each represents a hydrogen atom, the resulting azetidin-2-one derivative of formula (2) carries a vinylidene group as $R^7$. When starting with the compound of formula (1) wherein either one of $R^2$ and $R^3$ is an alkyl group with the other being a hydrogen atom, $R^7$ in the resulting compound of formula (2) becomes a vinylidene group or an acetylene group. When both of $R^2$ and $R^3$ are an alkyl group, $R^7$ becomes a vinylidene group.

The palladium complex which can be used in the present invention serves as a catalyst. A palladium compound and a ligand may be separately supplied to the reaction system to form a complex in situ. Any palladium compound can be used as long as it is capable of forming zerovalent palladium as an active species in the reaction system. Examples of such palladium compounds include divalent compounds, e.g., palladium(II) acetate, palladium(II) chloride, and palladium(II) acetylacetonate; and zerovalent compounds, e.g., tribenzylidene dipalladium and tetrakistriphenylphosphine palladium. Examples of suitable ligands to be used include trialkylphosphines, e.g., triethylphosphine and tributylphosphine; triarylphosphines, e.g., triphenylphosphine and tri(tolyl)phosphine; and trialkyl phosphites, e.g., triethyl phosphite and 4-ethyl-2,6,7-trioxa-1-phosphabicyclo[2.2.2]-octane. Particularly preferred of them is 4-ethyl-2,6,7-trioxa-1-phosphabicyclo[2.2.-2]octane.

4-Ethyl-2,6,7-trioxa-1-phosphabicyclo[2.2.2]octane can be synthesized by the process disclosed in *J. Org. Chem.*, Vol. 25, pp. 663–665 (1960) as shown in the following reaction scheme, in which phosphorus trichloride is reacted with 1,1,1-tri(hydroxymethyl)propane in the presence of pyridine in a large quantity of an appropriate solvent as shown in reaction scheme H:

Reaction Scheme H:

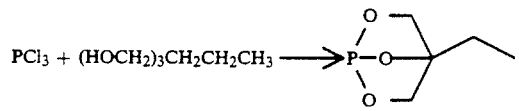

Since part of the ligand present together with a palladium compound is consumed for reducing divalent palladium to zero-valent palladium, it is recommended to increase the relative amount of the ligand with respect to the palladium compound to thereby ensure a high yield. More specifically, the ligand is preferably used in a relative amount of from 1 to 5 times, and particularly from 1 to 3 times, the amount of the palladium compound.

Where the protective group for an amino group in the starting compound of formula (1) is such a group as becoming an acid when released, e.g., a tosyl group, it is preferable that the reaction be carried out in the co-presence of a base, e.g., potassium carbonate and sodium carbonate.

The reaction is usually carried out by stirring the propargyl alcohol derivative of formula (1), a palladium compound, and a ligand in an appropriate solvent in a carbon monoxide atmosphere at a carbon monoxide pressure of from 1 to 50 atm, and preferably from 1 to 20 atm, at a temperature of from room temperature to 100° C., and preferably from room temperature to 80° C., for a period of from 2 to 20 hours, and preferably from 5 to 16 hours.

Examples of suitable solvents for the reaction include tetrahydrofuran (THF), dimethylformamide (DMF), acetonitrile, dioxane, dimethyl sulfoxide (DMSO), propanol, and butanol, with THF, DMF, and acetonitrile being preferred.

The palladium compound is used in an amount of from 0.001 to 1.0 mole, and preferably from 0.01 to 0.2 mole, per mole of the propargyl alcohol derivative of formula (1).

The process of the present invention holds an industrial advantage of producing azetidin-2-one derivatives, useful intermediates of penem antibiotics, through one reaction step in good yield.

The present invention is now illustrated in greater detail with reference to the following reference examples and examples, but it should be understood that the present invention is not deemed to be limited thereto. All the percents are by weight unless otherwise indicated.

REFERENCE EXAMPLE 1

Synthesis of
5-Hydroxy-2-methyl-2-tosylamino-3-dodecyne

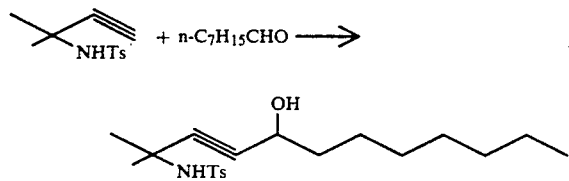

In 2 ml of THF was dissolved 1.185 g (5 mmole) of 3-methyl-3-tosylamino-1-butyne, and a THF solution of ethylmagnesium bromide (12 mmole) was added thereto at room temperature, followed by refluxing for 1 hour. After cooling the solution to 0° C., a solution of 1.25 ml (8 mmole) of n-octanal in 3 ml of THF was added thereto, and the mixture was stirred at room temperature for 2 hours. Water was added to the reaction mixture, and the mixture was extracted with ethyl acetate. The extract was washed successively with a hydrochloric acid aqueous solution, a sodium hydrogencarbonate aqueous solution, and water, and then dried. The solvent was removed by distillation, and the residual oily substance was purified by column chromatography to obtain 1.37 g (percent yield: 75%) of 5-hydroxy-2-methyl-2-tosylamino-3-dodecyne.

REFERENCE EXAMPLE 2

Synthesis of
5-Methoxycarbonyloxy-2-methyl-2-tosylamino-3-dodecyne

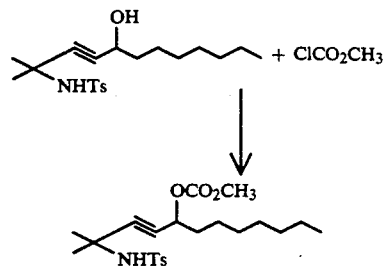

wherein Ts represents a tosyl group.

In 10 ml of THF was dissolved 1.37 g (3.76 mmole) of the 5-hydroxy-2-methyl-2-tosylamino-3-dodecyne obtained in Reference Example 1, and a THF solution of ethylmagnesium bromide (8.27 mmole) was added thereto, followed by stirring for 40 minutes. To the mixture was added dropwise 0.668 ml (8.65 mmole) of methyl chloroformate, and stirring was further continued for 50 minutes. Water was added thereto, and the mixture was extracted with ethyl acetate. The extract was washed successively with a hydrochloric acid aqueous solution, a sodium hydrogencarbonate aqueous solution, and water, and then dried. The solvent was removed by distillation, and the residual oily substance was purified by column chromatography to obtain 1.37 g (percent yield: 86%) of 5-methoxycarbonyloxy-2-methyl-2-tosylamino-3-dodecyne.

$^1$H-NMR (400 MHz, CDCl$_3$, δ): 0.98 (3H, d, J=1.10 Hz, CH$_3$), 0.99 (3H, d, J=1.46 Hz, CH$_3$), 1.30–1.50 (1H, brs, NH), 1.80–1.90 (1H, m, CH), 3.19–3.24 (1H, m, NCH), 3.78 (1H, d, J=13.0 Hz, CH), 3.81 (3H, s, OCH$_3$), 4.00 (1H, d, J=13.0 Hz, CH), 4.80 (2H, d, J=1.47 Hz, CH$_2$O), 7.20–7.40 (5H, m, aromatic protons).

REFERENCE EXAMPLE 3

Synthesis of
4-Benzylamino-1-t-butyldimethylsilyloxy-5-methyl-2-hexyne

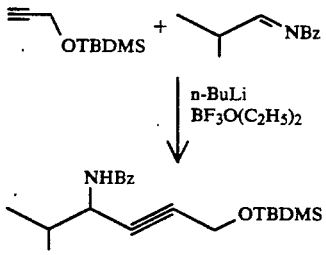

wherein TBDMS represents a t-butyldimentylsilyl group; n-Bu represents an n-butyl group; and Bz represents a benzyl group.

In 20 ml of THF was dissolved 1.87 g (11 mmole) of 3-t-butyldimethylsilyloxy-1-propyne, and 11.6 mmole of n-butyllithium was added thereto at −83° C. over 10 minutes, followed by stirring for 30 minutes. To the solution was added dropwise 1.43 ml (11.6 mmole) of boron trifluoride ethyl etherate, followed by stirring for 10 minutes. Then, a solution of 886 mg (5.5 mmole) of isobutylidenebenzylamine in 2 ml of THF was added to the solution at −83° C., the mixture was stirred at room temperature for 1 hour, and the reaction was stopped by addition of 15 ml of a 10% sodium hydroxide aqueous solution. The reaction mixture was extracted three times with 25 ml portions of diethyl ether, and the extracted organic layer was dried over anhydrous magnesium sulfate. The solvent was removed by distillation, and the residual oily substance was purified by silica gel column chromatography to obtain 1.64 g (percent yield: 90%) of 4-N-benzylamino-1-t-butyldimethylsilyloxy-5-methyl-2-hexyne.

REFERENCE EXAMPLE 4

Synthesis of 4-(N-Benzyl-N-t-butoxycarbonyl)amino-5-methyl-2-hexyn-1-ol

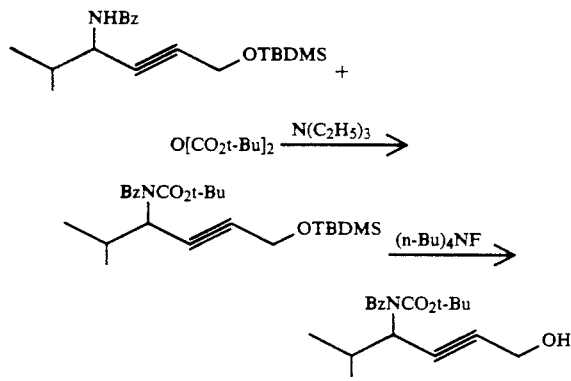

wherein t-Bu represents a t-butyl group; and Bz, TBDMS, and n-Bu are as defined above.

In methylene chloride were reacted 2.26 g of 4-N-benzylamino-1-t-butyldimethylsilyloxy-5-methyl-2-hexyne and di-t-butyl bicarbonate in the presence of triethylamine in a usual manner to obtain 1.90 g (percent yield: 84%) of 4-(N-benzyl-N-t-butoxycarbonyl)amino-1-t-butyldimethylsilyloxy-5-methyl-2-hexyne. The resulting compound was allowed to react in THF in the presence of tetra(n-butyl)ammonium fluoride to obtain 1.26 g (percent yield: 90.6%) of 4-(N-benzyl-N-t-butoxycarbonyl)amino-5-methyl-2-Hexyn-1-ol.

REFERENCE EXAMPLE 5

Synthesis of 4-(N-Benzyl-N-t-butoxycarbonyl)amino-1-methoxycarbonyloxy-5-methyl-2-hexyne

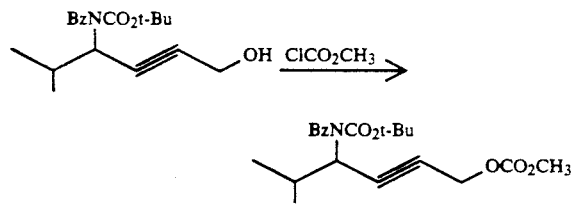

wherein Bz and t-Bu are as defined above.

In 4 ml of THF was dissolved 634 mg (2 mmole) of 4-(N-benzyl-N-t-butoxycarbonyl)amino-5-methyl-2-hexyn-1-ol, and a THF solution of ethylmagnesium bromide (2.4 mmole) was added thereto. Then, 0.31 ml (4 mmole) of methyl chloroformate was added thereto, followed by stirring at room temperature for 6 hours. The reaction mixture was extracted with ethyl acetate to obtain 679 mg (percent yield: 90.5%) of 4-N-benzyl-N-t-butoxycarbonyl)amino-1-methoxycarbonyloxy-5-methyl-2-hexyne.

REFERENCE EXAMPLE 6

Synthesis of 4-N-Benzylamino-1-methoxycarbonyloxy-5-methyl-2-hexyne

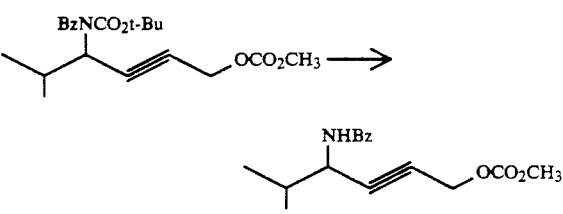

wherein Bz and t-Bu are as defined above.

In 6 ml of methylene chloride was dissolved 1.49 g (3.96 mmole) of 4-(N-benzyl-N-t-butoxycarbonyl)amino-1-methoxycarbonyloxy-5-methyl-2-hexyne, and 1.23 ml (23.76 mmole) of trifluoroacetic acid was added thereto slowly at 0° C. by stirring at room temperature for 3 hours. The reaction mixture was worked up in a usual manner to obtain 987.4 mg (percent yield: 90.7%) of 4-N-benzylamino-1-methoxycarbonyloxy-5-methyl-2-hexyne as an oily substance $^1$NMR (400 MHz, CDCl$_3$, δ): 0.89 (3H, t, J=6.60 Hz, CH$_3$), 1.20–1.35 (10H, m, CH$_2$), 1.45–1.62 (2H, m, CH$_2$), 1.53 (6H, s, CH$_3$), 2.42 (3H, s, CH$_3$), 3.79 (3H, s, OCH$_3$), 4.75 (1H, brs, NH), 4.93 (1H, t, J=6.60 Hz, CHO), 7.29 (2H, d, J=8.06 Hz, aromatic protons), 7.78 (2H, d, J=8.06 Hz, aromatic protons).

EXAMPLE 1

Synthesis of N-Tosyl-3-(octan-1-yl)-4,4-dimethyl-azetidin-2-one (2a)

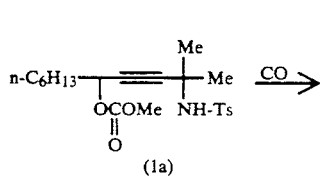

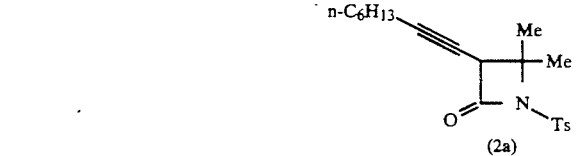

wherein Me and Ts are as defined above.

A mixture of 205 mg of compound (1a) (R$^1$: Me; R$^2$: H; R$^3$: n—C$_6$H$_{13}$; R$^4$, R$^5$: Me; R$^6$: Ts), 6 mg of palladium acetate, 8 mg of 4-ethyl-2,6,7-trioxa-1-phosphabicyclo[2.2.2]octane, 207 mg of potassium carbonate, and 2 ml of THF was allowed to react in a carbon monoxide atmosphere at 45° C. under atmospheric pressure for 6 hours. The reaction mixture was concentrated and purified by silica gel column chromatography to obtain 129 mg (percent yield: 71.5%) of compound (2a) as an oily substance.

IR (neat, cm$^{-1}$): 2925, 2850, 1795, 1785, 1600, 1450, 1360, 1242, 1205, 1165, 1085, 1020.

¹H-NMR (400 MHz, CDCl₃, δ): 0.87 (3H, t, J=6.59 Hz, CH₃), 1.18–1.37 (6H, m, CH₂), 1.37–1.50 (2H, m, CH₂), 1.58 (3H, s, CH₃), 1.64 (3H, s, CH₃), 2.14–2.20 (2H, m, CH₂), 2.45 (3H, s, CH₃), 3.70 (1H, t, J=2.56 Hz, CHCO), 7.35 (2H, d, J=8.1 Hz, aromatic), 7.90 (2H, d, J=8.1 Hz, aromatic).

¹³C-NMR (400 MHz, CDCl₃, δ): 89.7, 101.3, 127.3, 129:8, 136.7, 145.1, 161.4, 195.1.

EXAMPLE 2

Synthesis of N-Tosyl-3-(nonan-1-yl)-4,4-dimethylazetidin-2-one (2b)

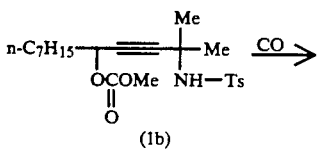

(1b)

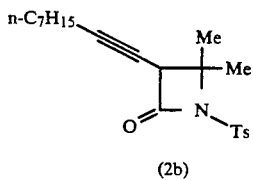

(2b)

wherein Me and Ts are as defined above.

A mixture of 218 mg of compound (1b) (R¹: Me; R²: H; R³: n—C₇H₁₅; R⁴, R⁵: Me; R⁶: Ts), 6 mg of palladium acetate, 17 mg of 4-ethyl-2,6,7-trioxa-1-phosphabicyclo[2.2.2]octane, 211 mg of potassium carbonate, and 2 ml of THF was allowed to react in a carbon monoxide atmosphere under atmospheric pressure for 7.5 hours. The reaction mixture was diluted with ethyl acetate, followed by filtration through Celite. The filtrate was concentrated, and the residue was purified by silica gel column chromatography to obtain 126.5 mg (percent yield: 66.2%) of compound (2b) as an oily substance.

¹H-NMR (400 MHz, CDCl₃, δ): 0 86 (3H, t, J=6.96 Hz, CH₃), 1.18–1.36 (8H, m, CH₂), 1.36–1.50 (2H, m, CH₂), 1.57 (3H, s, CH₃), 1.63 (3H, s, CH₃), 2.14–2.18 (2H, m, CH₂), 2.44 (3H, s, CH₃), 3.68 (1H, t, J=2.56 Hz, CHCO), 7.33 (2H, d, J=8.4 Hz, aromatic), 7.89 (2H, d, J=8.4 Hz, aromatic).

¹³C-NMR (400 MHz, CDCl₃, δ): 89.9, 102.3, 127.3, 12 9, 136.8, 145.1, 161.0, 195.0.

Elemental Analysis for C₂₁H₂₉O₃NS: Calcd. (%): C 67.17; H 7.78; N 3.73. Found (%): C 67.39, H 7.96, N 3.94.

EXAMPLE 3

Synthesis of N-Tosyl-3-(nonan-1-yl)-4,4-dimethylazetidin-2-one (2b)

Compound (2b) was obtained in the same manner as in Example 2, except for using triphenylphosphine as a ligand (percent yield: 30%).

EXAMPLE 4

Synthesis of N-Tosyl-3-vinylidene-4,4-dimethylazetidin-2-one (2c)

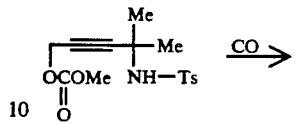

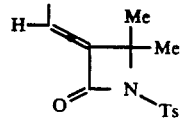

wherein Me and Ts are as defined above.

A mixture of 325 mg of compound (1c) (R¹: Me; R², R³: H; R⁴, R⁵: Me; R⁶: Ts), 22 mg of palladium acetate, 32 mg of 4-ethyl-2,6,7-trioxa-1-phosphabicyclo[2.2.2]octane, 211 mg of potassium carbonate, and 2 ml of THF was allowed to react at 50° C. at a carbon monoxide pressure of 10 atm for 6.5 hours. The reaction mixture was worked up in the same manner as in Example 2 to obtain 57.7 mg (percent yield: 20.8%) of compound (2c).

¹H-NMR (400 MHz, CDCl₃, δ): 1.67 (6H, s, CH₃), 2.44 (3H, s, CH₃), 5.42 (2H, s, C=CH₂), 7.34 (2H, d, J=8.1 Hz, aromatic), 7.91 (2H, d, J=8.1 Hz, aromatic).

¹³C-NMR (400 MHz; CDCl₃, δ): 21.6, 25.1, 71.0, 85.1, 110.8, 115.0, 127.1, 129.8, 137.2, 145.0, 158.2, 198.4.

EXAMPLE 5

Synthesis of N-Benzyl-3-vinylidene-4-isopropylazetidin-2-one (2d)

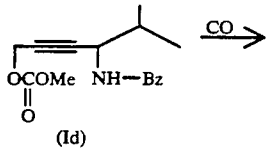

(1d)

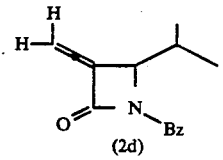

(2d)

wherein Me and Bz are as defined above.

A mixture of 226 mg of compound (1d) (R¹: Me; R², R³: H; R⁴: H; R⁵: isopropyl; R⁶: Bz), 18 mg of palladium acetate, 24 mg of 4-ethyl-2,6,7-trioxa-1-phosphabicyclo[2.2.2]octane, and 2 ml of THF was allowed to react at 50° C. at a carbon monoxide pressure of 10 atm for 5 hours. The reaction mixture was worked up in the same manner as in Example 2 to obtain 70.1 mg (percent yield: 37.8%) of compound (2d).

IR (neat, cm⁻¹): 3060, 3040, 2960, 1995, 1975, 1755, 1740, 1610, 1500, 1455, 1380, 1350, 1262, 1175, 1110, 1070, 1030, 970, 863.

¹H-NMR (400 MHz; CDCl₃; δ): 0.89 (3H, d, J=6.60 Hz, CH₃), 0.94 (3H, d, J=6.60 Hz, CH₃), 1.92–2.02 (1H, m, CH), 3.98–3.99 (1H, m, CHN), 4.11 (1H, d, J=15.4 Hz, CHN), 4.81 (1H, d, J=15.4 Hz, CHN), 5.24 (1H, s,

C=CH), 5.25 (1H, s, C=CH), 7.20-7.40 (5H, m, aromatic) $^{13}$C-NMR (400 MHz, CDCl$_3$, δ): 16.7, 18.9, 29.7, 45.3, 64.5, 82.0, 104.2, 112.1, 127.7, 128.1, 128.2, 128.8, 135.7, 163.1, 197.2

EXAMPLE 6

Synthesis of N-Benzyl-3-vinylidene-4-isopropylazetidin-2-one (2d)

A mixture of 138 mg (0.5 mmole) of compound (1d) as used in Example 5, 11 mg (0.05 mmole) of palladium acetate, 24 mg (0.15 mmole) of 4-ethyl-2,6,7-trioxa-1-phosphabicyclo[2.2.2]octane, and 3 ml of THF was allowed to react at 50° C. at a carbon monoxide pressure of 10 atm for 7 hours. The reaction mixture was worked in the same manner as in Example 2 to obtain 54.5 mg (percent yield: 48%) of β-lactam compound (2d).

EXAMPLE 7

Synthesis of N-Benzyl-3-(n-heptylvinylidene-4-isopropylazetidin-2-one (2 3)

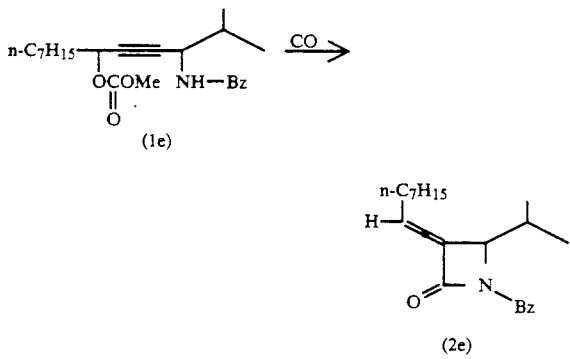

wherein Me and Bz are as defined above.

A mixture of 262 mg (0.7 mmole) of compound (1e) (R$^1$: Me; R$^2$: n—C$_7$H$_{15}$; R$^3$: H; R$^4$: isopropyl; R$^5$: H; R$^6$: Bz), 16 mg (0.07 mmole) of palladium acetate, 23 mg (0.14 mmole) of 4-ethyl-2,6,7-trioxa-1-phosphabicyclo[2.2.2]octane, and 3 ml of acetonitrile was allowed to react at 50° C. at a carbon monoxide pressure of 10 atm for 16 hours to obtain 116.5 mg (percent yield: 51%) of compound (2e).

$^1$H-NMR (400 MHz; CDCl$_3$; δ): 0.85-0.94 (9H, m, CH$_3$), 1.20-1.53 (10H, m, CH$_2$), 1.90-2.00 (1H, m, CH), 2.08-2.18 (2H, m, C=CCH$_2$), 3.93-3.95 (1H, m, CHN), 4.12 (1H, d, J=15.4 Hz, CHN), 4.79 (1H, d, J=15.4 Hz, CHN), 5.66 (1H, t, J=6.96 Hz, C=CH), 7.23-7.40 (5H, m, aromatic).

$^{13}$C-NMR (400 MHz, CDCl$_3$, δ): 98.7, 104.5, 104.6, 127.5, 128.1, 128.6, 135.7, 135.8, 163.9, 193.4, 193.5.

While the invention has been described in detail and with reference to specific examples thereof, it will be apparent to one skilled in the art that various changes and modifications can be made therein without departing from the spirit and scope thereof.

What is claimed is:

1. A process for preparing an azetidin-2-one derivative represented by formula (2):

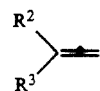

wherein R$^4$ and R$^5$, which may be the same or different, each represents a hydrogen atom, an alkyl group having from 1 to 8 carbon atoms, or an alkyl group having from 1 to 8 carbon atoms substituted with an alkoxy group, and acyl group represented by the formula RCO—where R is a hydrogen atom, an aliphatic group, an alicyclic group or an aromatic group, or an alkoxycarbonyl group; R$^6$ represents a protective group for an amino group; and R$^7$ represents a vinylidene group of formula

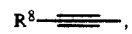

or an actylene group of formula

R$^8$—≡—, wherein R$^2$ and R$^3$, which may be the same or different, each represents a hydrogen atom or an alkyl group having from 1 to 8 carbon atoms; and R$^8$ represents an alkyl group having from 1 to 8 carbon atoms corresponding to R$^2$ or R$^3$, which comprises reacting a propargyl alcohol derivative represented by formula (1):

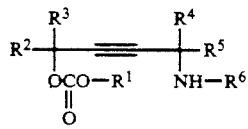

wherein R$^1$ represents an alkyl group having from 1 to 6 carbon atoms, a phenyl group, or a halogen-substituted phenyl group; R$^2$, R$^3$, R$^4$, R$^5$ and are as defined above, with carbon monoxide in the presence of a palladium complex, wherein said palladium complex is a complex formed in situ from a palladium compound and a ligand, and wherein said ligand is selected from the group consisting of trialkylphosphines, triarylphosphines, and trialkylphosphites, with the proviso that when both R$^2$ and R$^3$ in formula (1) are hydrogen atoms or alkyl groups having from 1 to 8 carbon atoms, R$^7$ in formula (2) represents the group

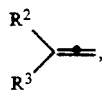

and when one of R$^2$ and R$^3$ in formula (1) is an alkyl group having from 1 to 8 carbon atoms and the other is a hydrogen atom, R$^7$ in formula (2) represents the group

or the group

2. A process for preparing an azetidin-2-one derivative represented by formula (2):

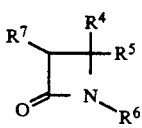

wherein $R^4$ and $R^5$, which may be the same or different, each represents a hydrogen atom, an alkyl group having from 1 to 8 carbon atoms, or an alkyl group having from 1 to 8 carbon atoms substituted with an alkoxy group, and acyl group represented by the formula RCO— where R is a hydrogen atom, an aliphatic group, an alicyclic group or an aromatic group, or an alkoxycarbonyl group; $R^6$ represents a protective group for an amino group; and $R^7$ represents a vinylidene group of formula

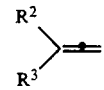

or an actylene group of formula

wherein $R^2$ and $R^3$, which may be the same or different, each represents a hydrogen atom or an alkyl group having from 1 to 8 carbon atoms; and $R^8$ represents an alkyl group having from 1 to 8 carbon atoms corresponding to $R^2$ or $R^3$, which comprises reacting a propargyl alcohol derivative represented by formula (1):

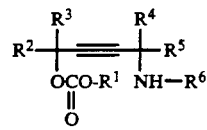

wherein $R^1$ represents an alkyl group having from 1 to 6 carbon atoms, a phenyl group, or a halogen-substituted phenyl group; $R^2$, $R^3$, $R^4$, $R^5$ and $R^6$ are as defined above, with carbon monoxide in the presence of a palladium complex, wherein said palladium complex is a complex formed in situ from a palladium compound and 4-ethyl-2,6,7-trioxa-1-phosphabicyclo[2.2.2]-octane, with the proviso that when both $R^2$ and $R^3$ in formula (1) are hydrogen atoms or alkyl groups having from 1 to 8 carbon atoms, $R^7$ in formula (2) represents the group

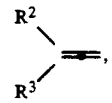

and when one of $R^2$ and $R^3$ in formula (1) is an alkyl group having from 1 to 8 carbon atoms and the other is a hydrogen atom, $R^7$ in formula (2) represents the group

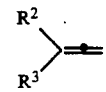

or the group

3. A process as claimed in claim 1, wherein the acyl group is selected from the group consisting of a formyl group, an acetyl group and a benzoyl group.

4. A process as claimed in claim 1, wherein said ligand is present in the reaction system in a relative amount of from 1 to 5 times the amount of the palladium compound.

5. A process as claimed in claim 1, wherein the protective group for an amino group represented by $R^6$ is selected from the group consisting of a benzyl group, a tosyl group, an acyl group, a p-methoxybenzyl group, and a biphenylmethyl group.

6. A process as claimed in claim 1, wherein said palladium compound is selected from the group consisting of palladium (II) acetate, palladium (II) chloride, palladium (II) acetylacetonate, tribenzylidene dipalladium and tetrakistriphenylphosphine palladium.

* * * * *